United States Patent [19]

Hart et al.

[11] Patent Number: 5,630,946

[45] Date of Patent: May 20, 1997

[54] METHOD FOR PROCESSING A BIOLOGICAL FLUID INCLUDING LEUKOCYTE REMOVAL IN AN EXTRACORPOREAL CIRCUIT

[75] Inventors: Stephen Hart, Hants, England; Frank R. Pascale; Vlado I. Matkovich, both of Glen Cove, N.Y.

[73] Assignee: PALL Corporation, East Hills, N.Y.

[21] Appl. No.: 392,358

[22] Filed: Feb. 21, 1995

Related U.S. Application Data

[63] Continuation-in-part of Ser. No. 389,682, Feb. 15, 1995, abandoned.

[51] Int. Cl.$^6$ ..................................................... A61M 1/38
[52] U.S. Cl. ........................... 210/805; 210/767; 604/4; 604/5
[58] Field of Search ........................... 210/767, 805, 210/195.1, 195.2, 252, 257.1, 258, 418, 419, 420, 435, 503, 508; 604/4, 5, 190

[56] References Cited

U.S. PATENT DOCUMENTS

| | | |
|---|---|---|
| 3,383,163 | 5/1968 | Menashi . |
| 3,448,041 | 6/1969 | Swank . |
| 3,593,854 | 7/1971 | Swank ............................. 210/436 |
| 3,765,536 | 10/1973 | Rosenberg ........................ 210/446 |
| 3,935,111 | 1/1976 | Bentley ............................ 210/489 |
| 4,046,696 | 9/1977 | Mouwen .......................... 210/431 |
| 4,087,363 | 5/1978 | Rosemeyer et al. ............... 210/315 |

(List continued on next page.)

FOREIGN PATENT DOCUMENTS

| | | |
|---|---|---|
| 0155003 | 9/1985 | European Pat. Off. . |
| 0267286 | 5/1988 | European Pat. Off. . |
| 0315022 | 5/1989 | European Pat. Off. . |
| 0370584 | 5/1990 | European Pat. Off. . |
| 2042919 | 10/1980 | United Kingdom . |
| 2056301 | 3/1981 | United Kingdom . |
| 9304763 | 3/1993 | WIPO . |

OTHER PUBLICATIONS

Ratner, B.D., et al., "Plasma Deposition and Treatment For Bio-material Applications", Academic Press, Inc., pp. 464–516 (1990).

Kikugawa, K., et al., "Filter Columns For Preparation of . . . Transfusion", Vox Sanguinis, vol. 34, (1978), pp. 281–290.

Diepenhorst, P., et al., "removal of Leukocytes fro Whole Blood . . . Wool", Vox Sanguinis, vol. 23, (1972), pp. 308–320.

Patterson, R.H., et al, "Disposable Filter for Microemboli", JAMA, vol. 215, No. 1, Jan. 4, 1971, pp. 76–80.

(List continued on next page.)

*Primary Examiner*—John Kim
*Attorney, Agent, or Firm*—Leydig, Voit & Mayer

[57] ABSTRACT

A method for removing undesirable material including leukocytes from a biological fluid in an extracorporeal circuit comprises passing a leukocyte containing biological fluid from a patient into a container; passing a portion of biological fluid from the container through a recirculation loop including a filter assembly for removing leukocytes to leukocyte deplete the biological fluid and to pass the portion of leukocyte-depleted biological fluid into the container; passing additional leukocyte containing biological fluid from a patient into the container so that the additional fluid is mixed with leukocyte depleted biological fluid in the container to provide a mixture including leukocyte depleted and non-leukocyte depleted biological fluid; passing the mixture of biological fluid from the container; passing a portion of the mixture to the patient while passing another portion of the mixture through the recirculation loop.

13 Claims, 3 Drawing Sheets

U.S. PATENT DOCUMENTS

| | | | |
|---|---|---|---|
| 4,092,246 | 5/1978 | Kummer | 210/504 |
| 4,115,277 | 9/1978 | Swank | 210/436 |
| 4,116,845 | 9/1978 | Swank | 210/446 |
| 4,157,967 | 6/1979 | Meyst et al. | 210/449 |
| 4,214,014 | 7/1980 | Hofer et al. | |
| 4,243,531 | 1/1981 | Crockett et al. | 210/188 |
| 4,246,107 | 1/1981 | Takenaka et al. | 210/806 |
| 4,261,806 | 4/1981 | Asai et al. | 204/165 |
| 4,283,289 | 8/1981 | Meyst et al. | 210/448 |
| 4,294,594 | 10/1981 | Sloane, Jr. et al. | 210/436 |
| 4,330,410 | 5/1982 | Takenaka et al. | 210/767 |
| 4,416,777 | 11/1983 | Kuroda et al. | 210/446 |
| 4,445,991 | 5/1984 | Arbit | 204/168 |
| 4,488,954 | 12/1984 | Hatada et al. | 204/169 |
| 4,572,724 | 2/1986 | Rosenberg et al. | 210/472 |
| 4,615,694 | 10/1986 | Raines | 64/126 |
| 4,642,089 | 2/1987 | Zupkas et al. | 604/4 |
| 4,648,866 | 3/1987 | Malbrancq et al. | 604/5 |
| 4,662,906 | 5/1987 | Matkovich et al. | 210/436 |
| 4,690,762 | 9/1987 | Katsura | 210/436 |
| 4,701,267 | 10/1987 | Watanabe et al. | 210/806 |
| 4,726,901 | 2/1988 | Pall et al. | 210/496 |
| 4,743,371 | 5/1988 | Servas et al. | 210/188 |
| 4,758,337 | 7/1988 | Köhn et al. | 210/94 |
| 4,828,543 | 5/1989 | Weiss et al. | 604/4 |
| 4,828,698 | 5/1989 | Jewell et al. | 210/266 |
| 4,845,132 | 7/1989 | Masuoka et al. | 210/490 |
| 4,861,617 | 8/1989 | Pall et al. | 604/122 |
| 4,880,548 | 11/1989 | Pall et al. | 210/767 |
| 4,886,487 | 12/1989 | Solem et al. | 604/5 |
| 4,904,234 | 2/1990 | Shimomura et al. | 604/5 |
| 4,919,802 | 4/1990 | Katsura | 210/188 |
| 4,923,620 | 5/1990 | Pall et al. | 210/767 |
| 4,925,572 | 5/1990 | Pall et al. | 210/767 |
| 4,933,092 | 6/1990 | Aunet et al. | 210/729 |
| 4,936,998 | 6/1990 | Nishimura et al. | 210/638 |
| 4,948,628 | 8/1990 | Montgomery et al. | 427/39 |
| 4,963,260 | 10/1990 | Naio et al. | 210/446 |
| 4,964,984 | 10/1990 | Reeder et al. | 210/188 |
| 4,985,153 | 1/1991 | Kuroda et al. | 210/782 |
| 5,028,332 | 7/1991 | Ohnishi | 210/500.34 |
| 5,100,564 | 3/1992 | Pall et al. | 210/782 |
| 5,151,192 | 9/1992 | Matkovich et al. | 210/646 |
| 5,152,905 | 10/1992 | Pall et al. | 210/767 |
| 5,229,012 | 7/1993 | Pall et al. | 210/767 |
| 5,258,126 | 11/1993 | Pall et al. | 210/767 |
| 5,258,127 | 11/1993 | Gsell et al. | 210/767 |
| 5,266,219 | 11/1993 | Pall et al. | 210/767 |
| 5,362,406 | 11/1994 | Gsell et al. | 210/767 |
| 5,391,142 | 2/1995 | Sites et al. | 604/4 |
| 5,403,272 | 4/1995 | Deniega et al. | 604/4 |
| 5,437,624 | 8/1995 | Langley | 604/4 |
| 5,540,841 | 7/1996 | Gsell et al. | 210/435 |

OTHER PUBLICATIONS

Bando, K. et al., "Leukocyte depletion ameriorates . . . bypass" Journal of Thoracic & Cardiovascular Surgery, vol. 99, No. 5, May 1990, pp. 873–877.

Finney, R.S., et al., "Polymorphonuclear . . . Bypass", Current Surgery, vol. 46, No. 6, Nov./Dec. 1989, pp. 474–476.

Hall, T.S., et al., "The Role of Leukocyte . . . Ischemia", Current Surgery, vol. 44, No. 2, Mar./Apr. 1987, pp. 137–139.

Pillai, R., et al., "Leukocyte Depletion . . . Storage", Annals of Thoracic Surgery, vol. 50, No. 2, Aug. 1990, pp. 211–214.

Performance Characteristics of Bentley Duraflo II Treated Arterial Filters, Results of Lab Testing & Comparative Evaluation, Baxter (1990).

Pall RC50™ and RC 100™ Leukocyte Removal Filters, Pall Biomedical Products Corp., SRC50/RC100 Brochure, pp. 1–7 (undated).

Pall PL 100® Leukocyte Removal Filter, , Pall Biomedical Products Corp., S–PL100 Brochure Rev. E, pp. 1–7 (undated).

The Pall Blood Filter for Extracorporeal Service, Mar. 1984, E34C, 6 pages, Pall Biomedical Products Corporation, New York.

Intersept Extracorporeal Blood Filters, Surgikos, Johnson & Johnson, 4 pages (undated).

Gambro, Swank® Blood Filters Bibliography, 11 pages (undated).

The Pall EC Plus™ Filter, ECP–3840a, M6874M, Pall Corporation, pp. 3–7 (1985).

AutoVent–SP™, Autoventing Blood Filter, Pall Biomedical Products Corporation, 2 pages (1989).

METHOD FOR PROCESSING A BIOLOGICAL FLUID INCLUDING LEUKOCYTE REMOVAL IN AN EXTRACORPOREAL CIRCUIT

The present application is a continuation-in-part of U.S. patent application Ser. No. 08/389,682 entitled "Treatment of a Biological Fluid in an Extracorporeal Circuit" filed Feb. 15, 1995, abandoned which is incorporated by reference in its entirety.

TECHNICAL FIELD

This invention relates to methods, devices and systems for depleting undesirable material from a biological fluid in an extracorporeal circuit, wherein the biological fluid is withdrawn from a patient's cardiovascular system, undesirable material is removed, and the biological fluid, depleted of undesirable material, is returned to the cardiovascular system. In particular, the present invention provides for depleting leukocytes from blood in an extracorporeal circuit, wherein the blood can be passed at a flow rate through a filter assembly for removing leukocytes independently of the flow rate at which blood is returned to the patient.

BACKGROUND OF THE INVENTION

During a typical operation requiring extracorporeal circulation, blood from the cardiovascular system of the patient is taken from the patient and collected in a container such as a venous reservoir. Typically, a pump is used to withdraw the blood from the venous reservoir and then deliver it to a gas exchanger, such as an oxygenator, which serves as an external lung, as it exposes the blood to the appropriate percentage of oxygen. The gas exchanger, which may have more than one outlet, may be combined with a heat exchanger to also control the temperature of the blood. The blood is passed from one outlet of the gas exchanger and delivered to a blood filter, which removes gaseous microemboli, fat emboli, aggregates and microaggregates, and other debris. During some extracorporeal protocols, the blood filter comprises a filter assembly that also removes leukocytes from the blood. From the filter, the blood is usually returned via the arterial line directly to the vascular system of the patient.

Ancillary circuits, typically including one or more additional pumps and a small reservoir, may be used to salvage blood from the operative site. The salvaged blood is delivered to a cardiotomy reservoir where it can be stored until the surgeon returns the blood directly or indirectly through the gas exchanger to the patient's cardiovascular system. During some protocols, the blood is directed from the cardiotomy reservoir to the venous reservoir, and returned to the patient via the arterial line as described previously. Another circuit, the cardioplegia circuit, may be used so that blood exiting another outlet of the oxygenator can be treated with chemical compounds and/or cooled, and delivered to the heart, to arrest the contractions of the myocardium. At the appropriate time, the blood is treated with a less concentrated chemical compound and/or warmed, and delivered to the heart before normal contractions are re-instituted. By these protocols, the collected blood is salvaged and the need for supplemental blood replacement may be minimized.

As noted earlier, some protocols involving the extracorporeal circulation of blood provide for some leukocyte depletion of the blood. Leukocyte depletion may be desirable as leukocytes can be activated during extracorporeal circulation, leading to damage as these activated leukocytes contact internal organs, particularly ischemic tissues, i.e., tissues in which no blood is flowing such as the heart and lungs during certain surgical procedures. Moreover, exposure to the most common leukocyte, the granulocytic neutrophil, is undesirable, since this leukocyte has been implicated as the mediator of tissue destructive events in a variety of disorders, including, for example, reperfusion injury. Additionally, circulating leukocytes have been implicated in a variety of other undesirable effects, including, but not limited to, transfusion complications, and pulmonary edema.

However, while some protocols involving extracorporeal circulation may provide for blood filtration, and even provide for leukocyte depletion, these protocols may suffer from several drawbacks. For example, since the blood filter can be in the arterial line leading directly to the patient, a blockage in the filter could lead to an interruption in blood flow, which is undesirable. Accordingly, some protocols provide for bypassing the filter. However, while bypassing the filter allows blood flow back to the patient, the use of the bypass means that the undesirable material can no longer be removed from the blood by the filter.

Moreover, a surgeon may prefer to utilize a filter that provides for relatively inefficient removal of undesirable material to minimize the risk of blocking. Illustratively, since a more efficient filter, e.g., including at least one of finer fibers, increased surface area, smaller pores, and a more dense filter element, may exhibit an undesirably high pressure differential between the inlet and the outlet as the undesirable material accumulates in the filter, the surgeon may prefer to utilize a less efficient filter.

Additionally or alternatively, since some filter assemblies, especially leukocyte filters assemblies, may have larger hold up volumes, some surgeons may prefer to avoid "tying up" the larger volume of blood in the line leading directly to the patient. This tying up of a large volume of fluid may be undesirable when blood needs to be quickly returned to the patient.

Moreover, since some extracorporeal treatment protocols may include passing blood through the filter for several hours, e.g., from about 2 hours or less to about 10 hours or more, the fear of accumulating undesirable material over this indeterminate amount of time may lead some surgeons to err on the side of caution by utilizing a less efficient filter, rather than face the unacceptably high risk of clogging.

Additionally, typical extracorporeal treatment protocols fail to allow the surgeon to optimize blood flow rates and/or blood flow paths for different purposes, since so much of the blood is usually flowing through the filter and back to the patient. In some embodiments, it may be desirable to provide one rate and/or flow path for more efficient leukocyte depletion, and another rate and/or flow path for the optimum return of oxygenated blood to the patient. It may be desirable to recirculate blood through a leukocyte depletion filter assembly in a section of the circuit other than the section of the circuit leading directly back to the patient, so that some of the blood reaching the patient has even fewer leukocytes. Additionally, or alternatively, it may be desirable to provide leukocyte depletion at a particular point during the operation, e.g., before reperfusion; or to provide it during a plurality of points, rather than providing leukocyte depletion during the entire operation.

Accordingly, there is an unmet need in the art for methods, systems, and devices for providing increased efficiency in removing undesirable material, particularly leukocytes, from biological fluid in an extracorporeal circuit.

Moreover, there is a need in the art for methods, systems, and devices for providing efficient removal of undesirable material from biological fluid in an extracorporeal circuit while minimizing the risk that the flow of biological fluid back to the patient could be compromised.

The present invention provides for ameliorating at least some of the disadvantages of the prior art. These and other advantages of the present invention will be apparent from the description as set forth below.

SUMMARY OF THE INVENTION

In accordance with the invention, an extracorporeal circuit capable of allowing biological fluid to be withdrawn from a source such as a patient, passed through a filter assembly for removing undesirable material, particularly leukocytes, at one flow rate, and returned to the source at another flow rate, is provided. The extracorporeal circuit is capable of allowing flow through the leukocyte depletion filter assembly whenever such flow would be desirable during the extracorporeal treatment protocol, e.g., during the entire protocol, or during a part or parts of the protocol. For example, the extracorporeal circuit is capable of allowing flow through the leukocyte depletion filter assembly during the entire protocol, or only during reperfusion.

The extracorporeal circuit is also capable of allowing a portion of leukocyte depleted biological fluid to be recirculated through the leukocyte depletion filter to deplete the fluid of additional leukocytes before passing the fluid to the patient. The extracorporeal circuit is also capable of allowing a mixture of leukocyte depleted and non-leukocyte depleted biological fluid to be passed through the leukocyte depletion filter so that the non-leukocyte depleted biological fluid in the mixture can be leukocyte depleted, and the leukocyte depleted biological fluid in the mixture can be depleted of additional leukocytes before passing the fluid mixture to the patient.

In accordance with the invention, the leukocyte depletion filter assembly can be utilized or bypassed at any desired stage(s) of the extracorporeal treatment protocol. Thus, biological fluid can be easily and efficiently leukocyte depleted whenever leukocyte depletion is desirable. Additionally, leukocyte depletion can be enhanced by recirculating biological fluid through a leukocyte depletion filter assembly at any desired stage(s) of the extracorporeal treatment protocol.

Moreover, the present invention allows medical personnel to quickly and easily bypass a section of the extracorporeal circuit. This is especially advantageous and desirable as it can minimize the risk of an interruption in the flow of biological fluid to the patient.

In describing the present invention, the following terms are used as defined below.

(A) Biological Fluid: A biological fluid includes any treated or untreated fluid associated with living organisms, particularly blood, including whole blood, warm or cold blood, and stored or fresh blood; treated blood, such as blood diluted with at least one physiological solution, including but not limited to saline, nutrient, and/or anticoagulant solutions. Biological fluid also refers to blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid; and platelets separated from plasma and resuspended in physiological fluid. The biological fluid typically includes leukocytes. As used herein, blood product or biological fluid refers to the components described above, and to similar blood products or biological fluids obtained by other means and with similar properties.

(B) Undesirable material: The biological fluid may also include a number or variety of undesirable materials. The undesirable elements may be present in the fluid as a result of the storage condition or environment, normal metabolic processes, or due to the processing environment, or other causes. As used herein, undesirable material refers to leukocytes, including activated and non-activated leukocytes; free gas, e.g., microemboli and gross bubbles; fat emboli; aggregates or microaggregates formed from platelets, leukocytes, red blood cells, and other debris; and debris from surgery, such as bone chips and lipids.

SPECIFIC DESCRIPTION OF THE INVENTION

The present invention provides a method for removing undesirable material including leukocytes from a biological fluid in an extracorporeal circuit comprising passing a biological fluid from a patient into a container, passing the biological fluid from the container through a filter assembly for removing leukocytes, and, passing a portion of the leukocyte depleted biological fluid toward the patient while passing another portion of the leukocyte depleted biological fluid toward the container. In some embodiments, the method includes passing a portion of the leukocyte depleted biological fluid toward the patient while passing the remainder of the leukocyte depleted biological fluid toward the container.

The present invention also provides a method for removing undesirable material including leukocytes from a biological fluid in an extracorporeal circuit comprising passing a biological fluid from a patient into a container, passing the biological fluid from the container through a filter assembly for removing leukocytes, passing the leukocyte depleted biological fluid to the container, and, passing at least a portion of the leukocyte depleted biological fluid from the container toward the patient.

The present invention also provides a method for removing undesirable material including leukocytes from a biological fluid in an extracorporeal circuit comprising passing a biological fluid from a patient into a container, passing the biological fluid from the container through a filter assembly for removing leukocytes, passing the leukocyte depleted biological fluid to the container, and, passing at least a portion of the leukocyte depleted biological fluid from the container toward the patient. In some embodiments, the method includes passing a portion of leukocyte depleted fluid toward the filter assembly while passing another portion of leukocyte depleted fluid toward the patient.

Methods according to the invention provide for continuously withdrawing a biological fluid from a patient into the container and returning the biological fluid from the container to the patient.

A method for removing undesirable material including leukocytes from a biological fluid in an extracorporeal circuit in accordance with the invention comprises passing a biological fluid from a patient into a container, wherein the container is in fluid communication with a leukocyte depletion filter assembly downstream of the container, and wherein at least a first pump and a second pump are arranged downstream of the container; operating the first pump to pass biological fluid from the container through the leukocyte depletion filter assembly, thereby depleting leukocytes from the biological fluid; and operating the second pump to pass leukocyte depleted biological fluid to the patient.

The present invention provides a method for removing undesirable material including leukocytes from a biological fluid in an extracorporeal circuit comprising continuously withdrawing a biological fluid from a patient into the container, and returning the biological fluid from the container to the patient, wherein, at least once, withdrawing the fluid and returning the fluid includes: passing the biological fluid from the container through a filter assembly for removing leukocytes; and, passing a portion of the leukocyte depleted biological fluid toward the patient and passing another portion of the leukocyte depleted biological fluid toward the container. The biological fluid passing toward the patient may include a mixture of leukocyte depleted biological fluid and non-leukocyte depleted biological fluid.

In some embodiments, withdrawing the fluid and returning the fluid includes passing the biological fluid from the container through a filter assembly for removing leukocytes; and, passing a portion of the leukocyte depleted biological fluid toward the patient while passing the remainder of the leukocyte depleted biological fluid toward the container.

The present invention provides method for removing undesirable material including leukocytes from a biological fluid in an extracorporeal circuit comprising: passing a biological fluid containing leukocytes from a patient into a container; passing a portion of biological fluid from the container through a recirculation loop including a filter assembly for removing leukocytes so that leukocyte-depleted biological fluid is passed into the container; passing additional leukocyte containing biological fluid from a patient into the container so that the additional fluid is mixed with the portion of leukocyte depleted biological fluid in the container to provide a mixture including leukocyte depleted and non-leukocyte depleted biological fluid; passing the mixture of biological fluid from the container; passing a portion of the mixture toward the patient while passing another portion of the mixture through the recirculation loop.

The present invention provides a method for processing biological fluid in an extracorporeal circuit comprising: mixing a non-leukocyte depleted biological fluid with a biological fluid depleted of leukocytes to provide a mixture including leukocyte depleted and non-leukocyte depleted biological fluid; passing a portion of the mixture toward a patient while passing another portion of the mixture through a recirculation loop including a filter assembly for removing leukocytes.

The present invention provides a system for processing biological fluid suitable for use in an extracorporeal circuit comprising at least one container suitable for containing a biological fluid; a recirculation circuit in fluid communication with the container, said circuit including: at least a first conduit, a second conduit, and a third conduit, said first, second, and third conduits each having a first end and a second end, wherein the first end of the first conduit and the first end of the second conduit are both in fluid communication with the container; a connector interposed between the second end of the second conduit and the first end of the third conduit, and in fluid communication therewith, said connector allowing fluid communication with a fourth conduit; a biological fluid processing assembly capable of depleting undesirable material from a biological fluid, said assembly comprising an inlet and an outlet and a porous medium interposed between the inlet and the outlet, and defining a fluid flow path between the inlet and the outlet and across the porous medium, wherein the second end of the first conduit is in fluid communication with the inlet, and the second end of the third conduit is in fluid communication with the outlet; wherein said connector allows fluid to be passed along the recirculation circuit and diverted from the recirculation circuit along the fourth conduit toward a patient.

The present invention provides a system for processing biological fluid suitable for use in an extracorporeal circuit comprising at least one container suitable for containing a biological fluid; a recirculation circuit in fluid communication with the container, said circuit including: at least a first conduit and a second conduit, said first conduit having a first end and a second end, and said second conduit having a first end and a second end, wherein the first end of the first conduit and the first end of the second conduit are both in fluid communication with the container; a biological fluid processing assembly capable of depleting undesirable material from a biological fluid, said assembly comprising an inlet and an outlet and a porous medium interposed between the inlet and the outlet, and defining a fluid flow path between the inlet and the outlet and across the porous medium, wherein the second end of the first conduit is in fluid communication with the inlet, and the second end of the second conduit is in fluid communication with the outlet; at least one connector in fluid communication with the second conduit, said connector allowing fluid to be passed along the recirculation circuit and diverted from the recirculation circuit.

The present invention provides a device for processing a biological fluid comprising at least one container for suitable for containing a biological fluid; a recirculation circuit in fluid communication with the container, said circuit including: a biological fluid processing assembly capable of depleting undesirable material from a biological fluid, said assembly comprising an inlet and an outlet and a porous medium interposed between the inlet and the outlet, and defining a fluid flow path between the inlet and the outlet and across the porous medium; wherein the recirculation circuit allows fluid to be passed from the container, through the processing assembly, and to the container.

In accordance with a method provided by the invention, during at least part of a extracorporeal treatment protocol, a biological fluid such as blood is withdrawn from the patient, collected in a container such as a venous reservoir, passed through a filter assembly for removing undesirable material, and returned to the patient. In some embodiments, the biological fluid depleted of undesirable material is mixed with biological fluid that has not been depleted of undesirable material, and this mixture is passed to the patient. Accordingly, the mixture that is passed to the patient contains a reduced level or amount of undesirable material.

Preferably, the filter assembly for removing undesirable material is a leukocyte depletion filter assembly, so that the biological fluid passed to the patient is leukocyte depleted biological fluid or a mixture of leukocyte depleted and non-leukocyte depleted biological fluid. If desired, a portion of the leukocyte depleted biological fluid exiting the filter assembly is passed to the container while a portion is passed to the patient.

Embodiments of the invention allow the mixing of leukocyte depleted biological fluid exiting the filter assembly and passing into the container, with non-leukocyte depleted biological fluid withdrawn from the patient and collected in the container. Some embodiments allow the mixing of leukocyte depleted and non-leukocyte depleted biological fluid in at least one conduit. Accordingly, embodiments of the invention allow for leukocyte depletion of non-leukocyte depleted biological fluid, while providing extra leukocyte depletion of some portions of leukocyte depleted biological fluid. This mixing of leukocyte depleted and non-leukocyte depleted biological fluid, e.g., blood, may be desirable, as it allows more of the biological fluid to be depleted of leukocytes before passing the fluid to the patient. Additionally, since the level or amount of leukocytes in the biological fluid as it is withdrawn from the patient may vary over the course of the extracorporeal protocol, it may be advantageous to be able to continually pass non-leukocyte depleted biological fluid through a leukocyte depletion filter assembly during an extracorporeal protocol.

Moreover, since the newly collected biological fluid in container 100 will typically have a higher concentration of leukocytes, the leukocyte depleted biological fluid passed through the leukocyte depletion assembly into the container can "dilute" the leukocyte concentration in newly collected biological fluid. Accordingly, this "diluted" or mixed biological fluid contains fewer leukocytes, and decreases the risk of "shocking" or "embarrassing" the heart when this fluid is passed to the patient.

In one embodiment, during part of the extracorporeal treatment protocol, most of the leukocyte depleted biological fluid exiting the filter assembly is passed toward the patient, e.g., via the arterial line, and the rest of the leukocyte depleted biological fluid is passed toward the container. In some embodiments, a portion of the biological fluid is recirculated from the container, through the filter assembly, and back to the container.

Embodiments of the invention provide for passing the leukocyte depleted fluid from the filter assembly into the container, passing a portion of leukocyte depleted fluid from the container toward the patient, while passing another portion of leukocyte depleted fluid from the container back through the filter assembly toward the container.

The extracorporeal circuit according to the invention allows fluid flow paths and/or flow rates to be varied as desired during the course of the extracorporeal treatment protocol. If desired, the biological fluid can be passed through the filter assembly at a flow rate similar to, identical to, or different than the flow rate for returning biological fluid, e.g., including leukocyte depleted biological fluid, to the patient.

If desired, during one stage or a plurality of stages of some embodiments of the treatment protocol, all of the biological fluid passing from the container and through the leukocyte depletion filter assembly can be returned to the patient directly. In some embodiments, during one stage or a plurality of stages of some embodiments of the treatment protocol, all of the biological fluid passing from the container can be returned to the patient directly.

During another stage or stages of some embodiments of the treatment protocol, some of the leukocyte depleted fluid exiting the filter assembly can be returned to the container, and the rest of the leukocyte depleted fluid exiting the filter assembly can be returned to the patient.

Of course, during another stage or stages of some embodiments of the treatment protocol, all of the leukocyte depleted fluid exiting the filter assembly is returned to the container and the leukocyte depleted fluid is mixed with non-leukocyte depleted fluid. Subsequently, a portion of this mixture of leukocyte depleted and non-leukocyte depleted fluid is passed to the patient, and another portion of the mixture is passed back to the container, e.g., through the filter assembly.

If desired, the biological fluid can be passed through the filter assembly at a different flow rate than the flow rate at which the leukocyte depleted fluid, by itself or part of a mixture, is returned to the patient.

In some embodiments, during at least one stage of the extracorporeal protocol, biological fluid may be passed from the container and returned to the patient without passing the fluid through the leukocyte depletion filter assembly.

Of course, in accordance with embodiments of the present invention, an extracorporeal treatment protocol may include any combination of stages, or all of the stages, referenced above.

In accordance with biological fluid systems according to the invention, biological fluid is passed through at least one biological fluid filter assembly for removing undesirable material, and passed to a patient. In the embodiments illustrated in FIGS. 1 through 5, biological fluid treatment system 300 allows biological fluid, e.g., blood, to be withdrawn from a patient through conduit 107, collected in a container 100 such as a venous reservoir or a combined venous reservoir/cardiotomy reservoir, passed through a biological fluid filter assembly 10 for removing undesirable material, preferably leukocytes, and returned to the patient, via conduit 106. In the embodiment illustrated in FIG. 6, biological fluid system 300 allows biological fluid, e.g., blood, to be withdrawn from a patient through conduit 107, collected in oxygenator 15 that also serves as a venous reservoir, passed through biological fluid filter assembly 10 for removing undesirable material, preferably leukocytes, and returned to the patient, via conduit 106.

Biological fluid processing system 300 can be utilized with a variety of other devices and apparatus. For example, at least one, and more preferably, at least two, pressure differential generators can be utilized to pass biological fluid from one location to another along the system 300. In all of the illustrated embodiments, pressure differential generators 1 and 2 comprise conventionally available pumps, such as peristaltic pumps.

The biological fluid processing system 300 illustrated in FIGS. 1, and 3–6, also includes a sub-circuit or loop 200, including a plurality of conduits, e.g., conduits 101, 102, and 103, which are preferably flexible tubing; and at least one connector 5, to allow fluid communication between the container 100 and the filter assembly 10. As illustrated, connector 5 includes three ports for the passage of fluid. If desired, fluid can be recirculated through the loop 200 and diverted from the loop 200. Typically, the operation of pressure differential generator 2 passes biological fluid through filter assembly 10, and the operation of pressure differential generator 1 passes fluid, preferably leukocyte depleted fluid, toward the patient.

Some embodiments including loop 200 allow, if desired, some, all, or none of the biological fluid exiting container 100 to be passed through biological fluid filter assembly 10 and to the patient. Illustratively, using, for example, FIG. 1 for reference, loop 200 allows, if desired, some, all, or none of the biological fluid exiting container 100 to be passed through biological fluid filter assembly 10 and then to the patient. Alternatively, using, for example, FIG. 3 for reference, loop 200 allows, if desired, some or none of the biological fluid exiting container 100 to be passed through biological fluid filter assembly 10 before passing it to the patient.

As will be noted in more detail below, in some embodiments, the loop or sub-circuit 200 is capable of allowing some of the fluid exiting assembly 10 to be recirculated back to the container 100, and the remainder of the fluid to be passed to the patient without recirculating this remainder through the container 100.

In other embodiments, the loop or sub-circuit 200 allows all of the fluid exiting assembly 10 to be passed into container 100. In these embodiments, loop 200 allows some fluid to be passed from container 100 and recirculated back through filter assembly 10 to the container 100, and some of the fluid to be passed from container 100 and to the patient without recirculating this fluid to the container 100.

Figure 1:
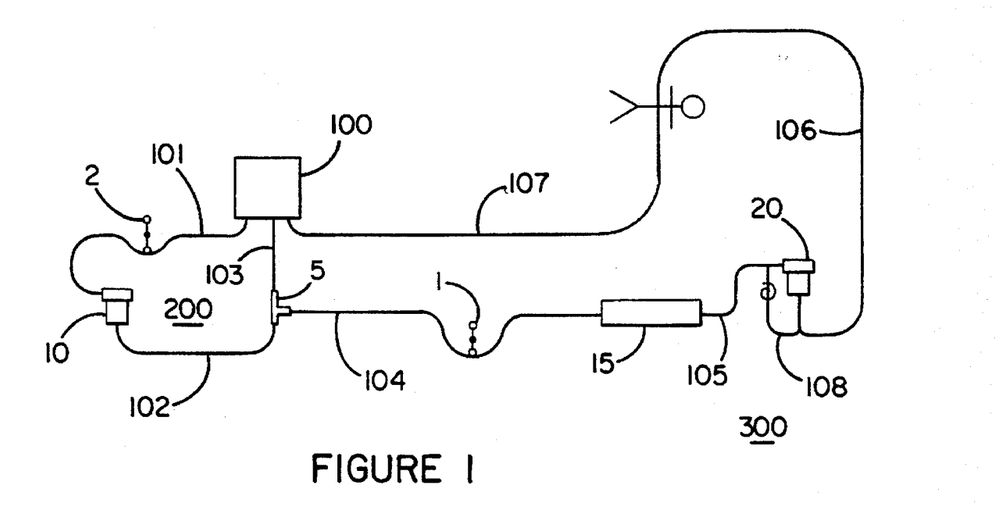
FIG. 1 is an embodiment of a system according to the present invention including a filter assembly for depleting leukocytes and other undesirable material.

Illustratively, using FIG. 1 for reference, with both pressure differential generators 1 and 2 operating, preferably with pressure differential generator 2 operating at a higher rate than pressure differential generator 1, some of the fluid exiting assembly 10 and passing along conduit 102 and through connector 5 is passed back to container 100 along conduit 103, and the rest of the fluid passing through connector 5 is passed out of loop 200 to the patient along conduits 104, 105, and 106. Some of the fluid is passing through conduit 103 back to the container 100 while some of the fluid is passing through conduit 104.

Figure 3:
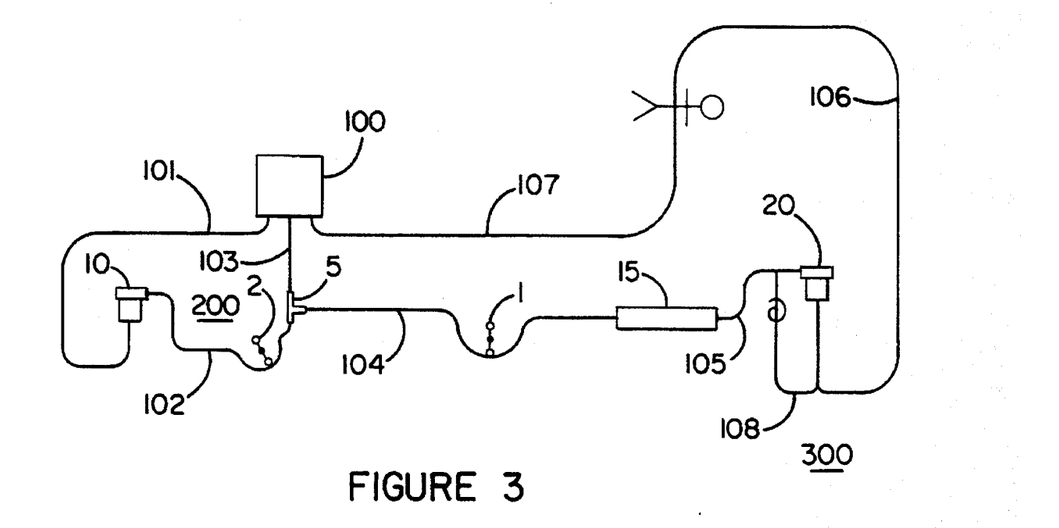
FIG. 3 is another embodiment of a system according to the present invention including a filter assembly for depleting leukocytes and other undesirable material.
Figure 4:
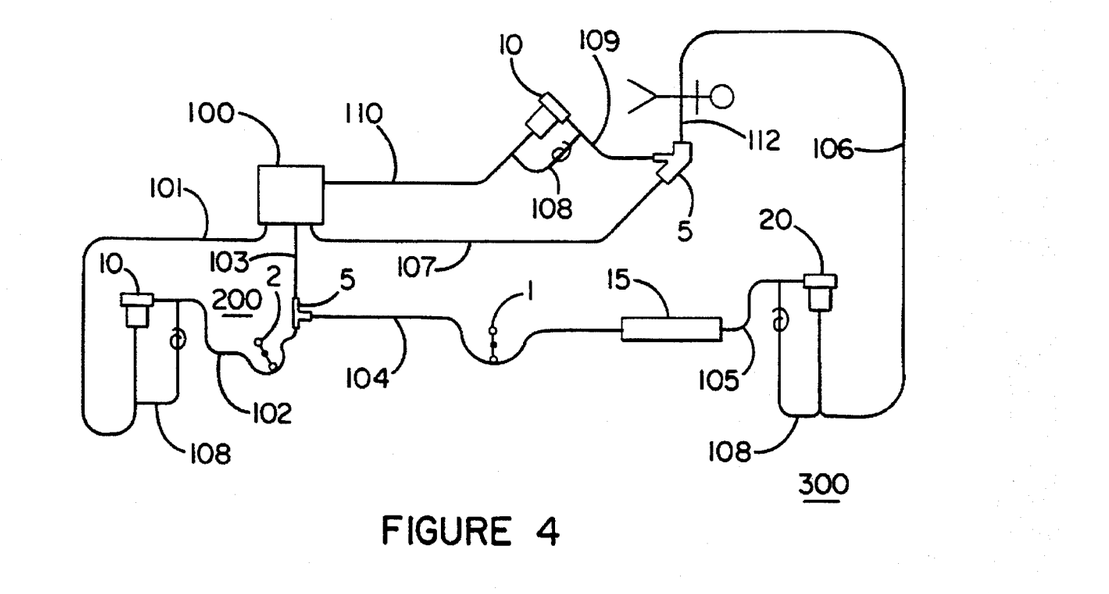
FIG. 4 is another embodiment of a system according to the present invention including a filter assembly for depleting leukocytes and other undesirable material, wherein two fluid flow paths are provided between the patient and a container such as a venous reservoir.

In other embodiments, using FIGS. 3 and 4 for reference, for example, with both pressure differential generator 2 and pressure differential generator 1 operating, some of the fluid exiting container 100 and passing through conduit 103 and connector 5 remains in the loop 200, and passes through conduit 102, filter assembly 10, conduit 101, and back to container 100; and some of the fluid exiting container 100 and passing through conduit 103 and connector 5 passes out of loop 200 to the patient along conduits 104, 105, and 106. Some of the fluid is passing through conduit 102 back toward the container 100 while some of the fluid is passing through conduit 104.

Figure 2:
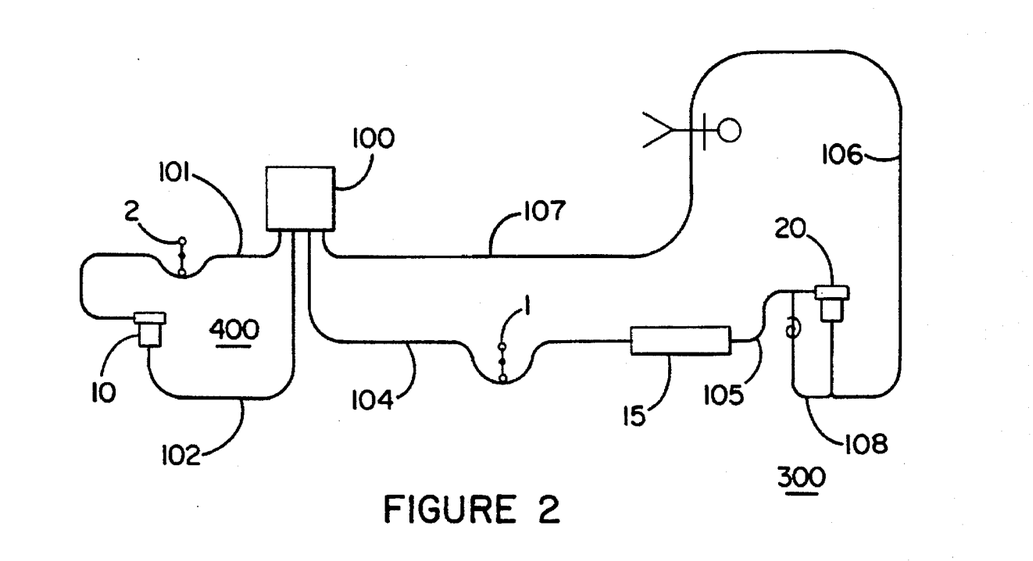
FIG. 2 is another embodiment of a system according to the present invention including a filter assembly for depleting leukocytes and other undesirable material.

In yet another embodiment, the biological fluid processing system 300 illustrated in FIG. 2 includes a sub-circuit or loop 400, including a plurality of conduits, e.g., conduits 101, and 102, which are preferably flexible tubing to allow fluid communication between the container 100 and the filter assembly 10. If desired, fluid can be recirculated through the loop. 400. Typically, the operation of pressure differential generator 2 passes biological fluid through filter assembly 10, and the operation of pressure differential generator 1 passes fluid, preferably leukocyte depleted fluid, toward the patient.

Loop 400 allows, if desired, some of the biological fluid exiting container 100 to be passed through biological fluid filter assembly 10 and to the patient. As will be noted in more detail below, the loop or sub-circuit 400 is capable of allowing the fluid exiting assembly 10 to be passed back to the container 100, and the leukocyte depleted fluid to be passed from the container 100 to the patient. Biological fluid can be recirculated through the loop 400.

Preferably, the system 300 as illustrated in the Figures includes, downstream of container 100, an oxygenator 15, which preferably also comprises a heat exchanger; and a biological fluid filter assembly 20. In all of the Figures, a bypass line for filter assembly 20 is also illustrated, i.e., conduit 108, along with a clamp associated with the bypass line. Typically, fluid filter assembly 20 provides for preventing free gas, e.g., microemboli and/or gross bubbles, from passing to the patient. Alternatively, or additionally, fluid filter assembly 20 may also provide for removing undesirable material other than free gas, e.g., fat emboli and/or aggregates, from the biological fluid.

In accordance with the invention, biological fluid can be withdrawn from the patient, passed through conduit 107 and collected in container 100. As noted earlier, biological fluid may be passed through biological fluid filter assembly 10 at any desirable time.

Using FIG. 1 for reference, with at least pressure differential generator 2 operating, preferably with pressure differential generator 1 also operating, biological fluid can be passed from container 100 into loop 200, through conduit 101, through assembly 10, and conduit 102, and, after passing through connector 5, passed to the patient through conduit 104, oxygenator 15, conduit 105, biological fluid filter assembly 20, and conduit 106 (the arterial line). Alternatively, biological fluid can be collected in container 100 and returned to the patient without passing through biological fluid filter assembly 10. Illustratively, for example with only pressure differential generator 1 operating, biological fluid can be passed from container 100 through conduit 103, connector 5, and then through conduit 104 and to the patient as described above. Of course, as noted earlier, when desired, a method according to the invention, typically including operating pressure differential generator 2 at a higher rate than pressure differential generator 1, includes passing some of the leukocyte depleted biological fluid through conduit 102 and connector 5 into conduit 103 toward container 100, while passing the remainder of the leukocyte depleted fluid through connector 5 into conduit 104 toward the patient.

Using FIG. 2 for reference, with both pressure differential generators 1 and 2 operating, biological fluid can be passed from container 100 into loop 400, through assembly 10, and the leukocyte depleted fluid is returned to container 100. Leukocyte depleted fluid is passed from container 100 to the patient through conduit 104, oxygenator 15, conduit 105, biological fluid filter assembly 20, and conduit 106 (the arterial line). Alternatively, biological fluid can be collected in container 100 and returned to the patient without passing into the loop 400 and through biological fluid filter assembly 10. Illustratively, with only pressure differential generator 1 operating, biological fluid can be passed from container 100 and then through conduit 104 and to the patient as described above.

Using FIG. 3 for reference, biological fluid can be passed from container 100 into loop 200, through conduit 103, and, after passing through connector 5, passed out of the loop 200, i.e., passed to the patient through conduit 104, oxygenator 15, conduit 105, biological fluid filter assembly 20, and conduit 106 (the arterial line). Accordingly, with, for example, only pressure differential generator 1 operating, biological fluid can be passed to the patient without passing through the biological fluid filter assembly 10 in the loop 200. Alternatively, biological fluid can be collected in container 100, and with both pressure differential generators 1 and 2 operating, a portion can be returned to the patient and another portion can be passed through biological fluid filter assembly 10. Illustratively, biological fluid can be passed from container 100 through conduit 103, and connector 5. The operation of pressure differential generator 1 allows some of the fluid passing through connector 5 to be diverted from the loop 200 and passed through conduit 104 toward the patient. The operation of pressure differential generator 2 allows some of the fluid passing through connector 5 to stay in the loop, i.e., to pass through connector 5 and conduit 102, through filter assembly 10, so that the leukocyte-depleted fluid can be passed through conduit 101, and back into container 100. Within the container 100, the leukocyte depleted fluid is mixed with the non-leukocyte depleted fluid, e.g., the non-leukocyte depleted fluid withdrawn from the patient and passed through conduit 107.

The components of the invention are described in more detail below.

A variety of biological fluid filter assemblies 10 for removing undesirable material, especially leukocytes, are suitable for carrying out the present invention. In some embodiments, in addition to removing leukocytes, filter assemblies 10 are capable of removing other undesirable material, including, but not limited to, free gas, fat emboli, aggregates, and debris. Illustrative suitable assemblies are disclosed in, for example, U.S. Pat. Nos. 5,258,127, 5,362, 406; International Publication Nos. WO 93/04763 and WO 95/03113; and copending U.S. patent application Serial No. 08/095,595 filed Jul. 26, 1993.

The biological fluid filter assembly 10 according to the present invention comprises a housing including an inlet and an outlet and defining a fluid flow path between the inlet and the outlet, and a porous medium, i.e., a filter element, interposed between the inlet and the outlet across the fluid flow path.

A variety of materials can be used for preparing the porous medium of the biological fluid filter assembly 10. Preferably, the porous medium is prepared from at least one polymeric material, more preferably, at least one synthetic polymeric material. Illustrative materials include, for example, polybutylene terephthalate (PBT), polyethylene, polyethylene terephthalate (PET), polypropylene, polymethylpentene, polychlorotrifluoro-ethylene, polyphenyl sulfide, poly(1,4-cyclohexylene dimethylene terephthalate), PETG (a polyester polymerized with an excess of glycol), nylon 6, nylon 66, nylon 612, nylon 11, and a nylon 6 copolymer described as "80% nylon 6 with 20% polyethylene-oxide-diamine."

In one preferred embodiment, the porous medium comprises a fibrous medium, typically a medium prepared from melt-blown fibers. The porous medium is preferably treated for increased efficiency in processing a biological fluid. For example, the medium may be surface modified to affect the critical wetting surface tension (CWST) of the medium, as described in, for example, U.S. Pat. No. 4,880,548. In some embodiments of the invention, the CWST may be modified as described in U.S. Pat. Nos. 4,880,548; 4,925,572; 5,152, 905; and 5,258,127.

Preferably, the porous medium or media according to the invention, which are, more preferably, porous fibrous media, have a CWST of greater than about 58 dynes/cm. For example, a fibrous medium may have a CWST in the range from about 60 dynes/cm to about 115 dynes/cm, e.g., in the range of about 61 to about 90 dynes/cm. In some embodiments, the fibrous medium has a CWST of about 62 dynes/cm, or greater, e.g., in. the range from about 63 to about 70 dynes/cm.

Surface characteristics of the media can be modified by chemical reaction including wet or dry oxidation, by coating or depositing a polymer on the surface, or by a grafting reaction. Grafting reactions may be activated by exposure to an energy source such as gas plasma, heat, a Van der Graff generator, ultraviolet light, electron beam, or to various other forms of radiation, or by surface etching or deposition using a gas plasma treatment. With respect to gas plasma treatments, typical processes utilize, for example, oxygen plasma, or a mixture of ammonia plasma and the plasma of an inert gas such as argon.

Preferably, the porous, fibrous medium is configured to provide a depth filter. More preferably, the fibrous depth filter has a hollow, cylindrical configuration. A hollow, cylindrical configuration is preferred as it presents a larger surface area to liquid flowing outside-in through the depth filter. This arrangement can allow undesirable material to spread more thinly around the filter, and minimize the possibility of accumulating sufficient material on the surface of the filter to block liquid flow.

The filter assembly can be configured in a variety of ways according to the invention. For example, the filter assembly may include a solid filter element which may have a disk-like or cylindrical shape and may be positioned in a housing to filter biological fluid flowing longitudinally or axially through the filter element. The inlet and outlet of the filter assembly would then communicate with opposite ends of the filter element and the side of the filter element would be sealed against the housing to prevent bypass of the fluid around the filter element.

Alternatively, the filter assembly may include a hollow filter element which may have a cylindrical shape as noted earlier. The element may be disposed in the housing to filter biological fluid flowing laterally or radially through the filter element. For example, to filter liquid flowing inside/out through the filter element; the inlet and outlet of the filter assembly would be arranged to respectively communicate with the interior and exterior of the hollow filter element.

The filter element, which preferably includes a fibrous porous medium, may comprise a plurality of layers. The filter element may also include additional structures such as, for example, end caps, edge seals, a cage, a core, and a wrap.

Illustratively, the filter element may include a wrap that surrounds the fibrous medium. The wrap may protect the fibrous medium from damage when the element is assembled. Typically, the wrap comprises a flexible, porous material, preferably having a relatively large pore size. For example, the wrap may comprise a sheet of spun-bonded, non-woven polypropylene fibers.

The filter element may include a porous element, e.g., disposed coaxially to the downstream surface of the fibrous medium, e.g., around the interior of the fibrous medium. The porous element is preferably fashioned from any compatible porous membrane or woven or non-woven material, including a mesh or a screen. The porous element can serve as, for example, a final filter to remove aggregates that escape the fibrous medium or form at the downstream portion of the fibrous medium.

Typically, the filter element includes a perforated core disposed within and adjacent to the interior of the porous element, and serves principally to support the fibrous medium and the porous element against the pressure differential across the filter element. Consequently, the perforated core may be fashioned from any suitable rigid material including a metal such as stainless steel or a rigid polymer such as polyolefin, polyester, or polyacrylate.

A variety of biological fluid filter assemblies 20 for removing undesirable material such as free gas (microemboli and gross bubbles) and/or other undesirable material, e.g., fat emboli; aggregates formed from platelets, leukocytes, red blood cells and other debris, are suitable for carrying out the present invention. One illustrative assembly is disclosed in, for example, U.S. Pat. No. 4,572,724.

The biological fluid filter assembly 20 according to the present invention comprises a housing including an inlet and an outlet and defining a fluid flow path between the inlet and the outlet, and a porous medium, i.e., a filter element, interposed between the inlet and the outlet across the biological fluid flow path.

The filter element may also include additional structures such as, for example, end caps, edge seals, a cage, a core, and a wrap.

Typically, the assembly 20 also includes a hydrophobic membrane that allows gas but not biological fluid to pass through the membrane and out of the assembly. Alternatively or additionally, the assembly 20 may include a sponge ring, preferably treated with an antifoaming agent. The sponge ring may capture small bubbles entrained in the biological fluid as the fluid passes through the sponge and cause the bubbles to coalesce and form larger bubbles that break away from the sponge and rise against the flow of the biological fluid, to increase the efficiency in separating gas from the fluid.

A variety of materials can be used for preparing the porous medium of the biological fluid filter assembly 20. Preferably, the porous medium is prepared from at least one synthetic polymeric material.

In some embodiments, biological fluid filter assemblies 10 and 20 may be similar, e.g., with respect to at least one of configuration, media, and surface treatment. Illustratively, assemblies 10 and 20 may comprise leukocyte depletion filter assemblies. The leukocyte depletion media may differ with respect to, for example, at least one of: number of layers, material utilized, CWST, surface treatment, fiber diameter, and surface area. Alternatively, or additionally, assemblies 10 and 20 may both provide for removal of free gas.

Moreover, in some embodiments, assembly 10 may also include a bypass line 108 and a clamp associated with the bypass line, similar to that illustrated with respect to assembly 20. The system 300 illustrated in FIG. 4, that includes two biological fluid filter assemblies 10, includes a bypass line 108 with each assembly 10. A bypass line can also be utilized with an assembly 10 in any embodiment of the invention, e.g., assemblies 10 in FIGS. 1–3, 5 and 6. Accordingly, existing assemblies that already have a bypass arrangement may be easily utilized in accordance with the invention. In some embodiments, a bypass line 108 associated with an assembly 10 may the system to be primed more efficiently, e.g., faster.

Typically, biological fluid filter assemblies 10 and 20 are each suitable for use in environments that require a flow rate capacity of at least about 1 liter/minute, preferably a capacity of at least about 2 liters/minute. During many extracorporeal treatment protocols, biological fluid filter assemblies 10 and 20 are each capable of removing undesirable material at a flow rate capacity of about 3 liters per minute, or more, at a differential pressure of less than about 15 p.s.i, more preferably, at a differential pressure of less than about 8 p.s.i. In some embodiments, biological fluid filter assemblies 10 and 20 are each capable of removing undesirable material at a flow rate capacity of about 6 liters per minute at a differential pressure of less than about 15 p.s.i, more preferably at a differential pressure of less than about 8 p.s.i.

A variety of conduits, containers, connectors, oxygenators and pumps are known in the art, and are commercially available.

As noted earlier, conduits 101, 102, 103, 104, 105, 106, 107, and 108, are preferably flexible tubing, as is known in the art. Connector 5 allows fluid to be recirculated through the loop 200 and diverted from the loop 200. Connector 5 includes at least three ports for the passage of fluid as is known in the art, e.g., a commercially available Y- or T-connector.

Container 100 is preferably a commercially available venous reservoir or combined venous reservoir/cardiotomy reservoir. The reservoirs may have inlet and/or outlet ports at the top, side(s), or bottom of the container as is known in the art. Additionally, while the illustrated embodiments show conduit 107 allowing fluid to be collected from the patient and passed into the container 100 through a separate port from that allowing fluid to be passed through the recirculation circuit into the container 100 (e.g., from conduit 101 in FIG. 3), it should be clear that other arrangements are also encompassed by the invention. For example, with respect to FIG. 3, a connector, e.g., a Y- or T-connector, may be in fluid communication with an inlet port of the container 100, and the downstream ends of conduits 101 and 107, so that fluid streams passing through conduits 101 and 107 pass through the Y- or T-connector and merge with their combined flow then passing via a single inlet port into container 100. This connector may be similar or identical to connector 5.

Oxygenator 15 is preferably a commercially available oxygenator, more preferably, a combined oxygenator/heat exchanger, as is known in the art. In some embodiments of the system 300, e.g., with respect to FIGS. 1–5, the oxygenator 15 preferably comprises a membrane oxygenator/heat exchanger as is known in the art.

As noted earlier, pressure differential generators 1 and 2 are preferably commercially available pumps, such as peristaltic pumps, as are known in the art.

Of course, the invention may include additional elements, components, and devices. For example, the invention may include at least one additional conduit (e.g., conduits 109, 110, 111, and 112) and/or at least one additional connector. The additional connector(s) may include two ports for the passage of fluid, or more than two ports. Accordingly, these additional connectors may allow connection between two conduits, e.g., a two port connector; or connection between three conduits, or more, e.g., a Y- or T-connector.

In accordance with the invention, pressure differential generators 1 and 2 may be operated at about the same rate, or at different rates. Accordingly, pressure differential generator 1 can be operated at a higher rate than pressure differential generator 2, or pressure differential generator 1 can be operated at a lower rate than pressure differential generator 2.

In accordance with some embodiments of the invention as illustrated in the Figures, biological fluid filter assembly 10 is easily bypassed if desired. For example, if the pressure differential between the inlet and the outlet of assembly 10 rises to an undesirable level, or if the assembly becomes blocked, the continued operation of pressure differential generator 1 ensures that blood will continue to pass from container 100 to the patient. Accordingly, blood will pass from container 100 and through conduit 103 (FIGS. 1, and 3–6) or conduit 104 (FIG. 2), and then to the patient. This bypass can be manually operated, e.g., by opening bypass line 108 in loop 200 as shown in, for example, FIG. 4. Alternatively, pressure differential generator 2 can be turned off, and the section of the extracorporeal circuit including the filter assembly 10 in the loop can be automatically avoided, as the fluid takes the path of least resistance from container 100 to conduit 104 (with respect to FIGS. 1 and 3–6), or the fluid takes the only available flow path from container 100 to conduit 104 (with respect to FIG. 2).

In one preferred embodiment according to the invention as illustrated in FIG. 1, providing leukocyte depletion for any desired period, pressure differential generator 2 is operated at a higher rate than pressure differential generator 1. Accordingly, biological fluid is passed through biological fluid filter assembly 10, which is a leukocyte depletion filter assembly, and a portion of the leukocyte depleted fluid passes toward the patient, i.e., along conduit 104, while the remainder of the leukocyte depleted fluid passes toward the container 100, i.e., along conduit 103. As the pressure differential generators 1 and 2 continue to operate, some of the fluid will recirculate from container 100, through the loop 200 including the leukocyte depletion filter assembly, and back into the container 100. Thus, some of the fluid, having passed through the leukocyte depletion filter assembly more than once, is more highly leukocyte depleted before being returned to the patient. In some embodiments, wherein pressure differential generator 2 is operating at a higher rate than pressure differential generator 1, more of the fluid can be leukocyte depleted before passing it to the patient. Of course, biological fluid may be repeatedly circulated through the loop 200.

In one preferred embodiment according to the invention as illustrated in FIG. 3, providing leukocyte depletion for any desired period, pressure differential generator 2 is operated at a higher rate than pressure differential generator 1. Accordingly, biological fluid is passed from container 100 into loop 200 through conduit 103 and connector 5. The operation of pressure differential generator 1 allows some of the fluid passing through connector 5 to be diverted from the loop 200 and passed through conduit 104 and to the patient. The operation of pressure differential generator 2 allows the other portion of the fluid passing through connector 5 to remain in the loop, passing through conduit 102, and filter assembly 10, wherein undesirable material is removed from the fluid. The biological fluid, depleted of undesirable material, e.g., leukocytes, passes through conduit 101 and back into container 100 where it is mixed with the non-leukocyte depleted fluid that passed into container 100 through conduit 107. As the pressure differential generators 1 and 2 continue to operate, some of the mixture including leukocyte-depleted fluid will pass from container 100, through connector 5, and then to the patient. Some of the mixture including leukocyte-depleted fluid passing from container 100 and passing through connector 5 will recirculated, i.e., passed through assembly 10 and back into container 100. Thus, some of the fluid, having passed through the leukocyte depletion filter assembly more than once, is more highly leukocyte depleted before being returned to the patient. In some embodiments, wherein pressure differential generator 2 is operating at a higher rate than pressure differential generator 1, more of the fluid can be leukocyte depleted before passing it to the patient. Of course, biological fluid may be repeatedly circulated through the loop 200.

In accordance with the invention, pressure differential generators 1 and 2 may be operated at about the same rate, or pressure differential generator 1 can be operated at a higher rate than pressure differential generator 2.

Using FIG. 1 for reference, in one embodiment of the invention, e.g., wherein pressure differential generators 1 and 2 are operated at about the same rate, some of the fluid is passed from container 100 through the leukocyte depletion filter assembly and directed toward the patient along conduit 104, and some of the fluid is passed from container 100 through conduit 103 and directed toward the patient along conduit 104. Accordingly, some of the biological fluid reaching the patient will be leukocyte depleted.

Similarly, using FIG. 3 for reference, in another embodiment of the invention, e.g., wherein pressure differential generators 1 and 2 are operated at about the same rate, some of the fluid passing from container 100 and through connector 5 is passed through conduit 102 and through the leukocyte depletion filter assembly into container 100 while some of fluid passing through connector 5 is directed toward the patient along conduit 104. As the pressure differential generators 1 and 2 continue to operate, some of the leukocyte depleted biological fluid is mixed with non-leukocyte depleted biological fluid in container 100. This mixture will be passed from the container and through connector 5. Some of this mixture, that includes leukocyte depleted fluid, will pass along conduit 102 toward the filter assembly 10, and some of this mixture, which also includes leukocyte depleted fluid, will pass along conduit 104 toward the patient. Accordingly, the biological fluid reaching the patient has a reduced level of leukocytes.

In accordance with the invention, e.g., using FIGS. 1–6 for reference, biological fluid will still be delivered to the patient if pressure differential generator 1 is operated at a higher rate than pressure differential generator 2. Accordingly, the present invention provides for delivering biological fluid to the patient without having to "match" the speeds of the pressure differential generators, e.g., the pumps.

As noted earlier, in accordance with some embodiments of the invention, an "automatic" bypass of biological fluid filter assembly 10 is provided.

Other embodiments are encompassed by the present invention. Illustratively, biological fluid may be passed through filter assembly 10 to remove leukocytes during cardioplegia. For example, while a cardioplegia circuit is not illustrated in the Figures, since the oxygenator 15 may have an additional outlet port, leukocyte depleted biological fluid exiting assembly 10 can be passed through connector 5, conduit 104, and oxygenator 15, and exit oxygenator 15 through two outlet ports, a first outlet port leading to conduit 105, and a second outlet port leading to a cardioplegia circuit. The leukocyte depleted biological fluid can be mixed with a chemical compound, and/or passed through a heat exchanger, before passing the fluid to the heart before re-initiating contractions, thus minimizing "embarrassment" or "shock" to the heart caused by direct exposure to leukocytes. Moreover, if desired, this cardioplegia circuit can also include a separate leukocyte depletion filter assembly, so that the fluid reaching the heart has been even further leukocyte depleted. Examples of cardioplegia circuits, including those having a separate leukocyte depletion filter assembly, are disclosed in copending U.S. application Ser. No. 08/095,595, and International Publication No. WO 95/03113.

In another embodiment, biological fluid remaining in the biological fluid filter assembly 10 at the completion of the extracorporeal treatment protocol may be recovered for later use. For example, with reference to the Figures, once the protocol has been completed, with the patient disconnected from the circuit and pumps 1 and 2 turned off, assembly 10 can be raised above the level of the container 100 to drain some of the fluid held up in assembly 10 and/or the upstream conduit (e.g., conduit 101 in FIG. 1, or conduit 102 in FIG. 3) back,into container 100. Inverting the assembly 10 may allow additional fluid to be drained. The fluid recovered in container 100 may be treated, e.g., cleaned to remove, for example, heparin, and the cleaned fluid, e.g., containing red cells, may be later administered to the patient, if desired.

In another embodiment, the biological fluid filter assembly for removing leukocytes can be arranged as part of a recirculation loop or subcircuit downstream of the oxygenator, preferably a bubbler oxygenator that also serves as a venous reservoir. As will be clear from the following description, the oxygenator/venous reservoir, that allows biological fluid to be collected, and allows leukocyte depleted fluid to be mixed with non-leukocyte depleted fluid, can be considered to be a container according to the present invention.

Figure 6:
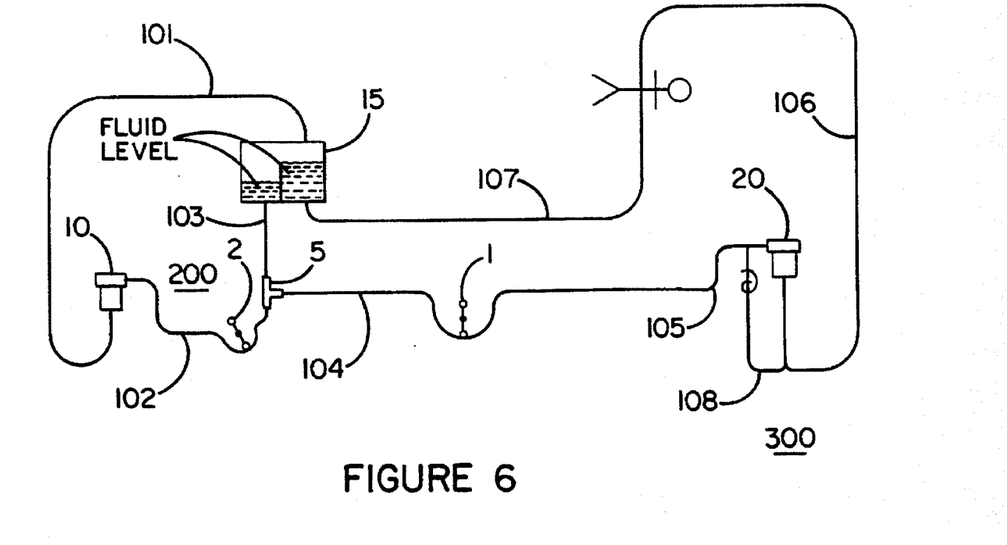
FIG. 6 is another embodiment of a system according to the present invention including a bubbler oxygenator for receiving a patient's biological fluid, and a filter assembly for depleting leukocytes and other undesirable material.

In the embodiment illustrated in FIG. 6, the oxygenator 15 preferably comprises bubbler oxygenator that also serves as a venous reservoir. Oxygen is delivered to the oxygenator through an oxygen filter (not shown). Blood withdrawn from the patient through conduit 107 enters the "venous" side of the oxygenator, and as the oxygenator fills to a certain level with blood, some of this blood passes into the "arterial" side of the oxygenator. The illustrated embodiment shows blood in both sides of the oxygenator.

Using FIG. 6 for reference, a recirculation loop 200 including a filter assembly for removing leukocytes 10, a plurality of conduits 101–107, and a three port connector 5, may be placed in fluid communication with an oxygenator 15, so that biological fluid entering the oxygenator can be passed into the loop, and, if desired, through the filter assembly 10. Illustratively, blood withdrawn from the patient and/or the cardiotomy reservoir and passed into oxygenator 15, e.g., through conduit 107, may be passed from the oxygenator, through conduit 103 of the recirculation loop 200, and through the connector 5, and diverted from the loop 200. Accordingly, blood may be returned to the patient along conduit 104 without passing through the filter assembly. Alternatively or additionally, blood may remain in the loop 200, and be passed along conduit 102, through the filter assembly 10, and conduit 101 into oxygenator 15, wherein leukocyte depleted blood is mixed with non-leukocyte depleted blood passed into oxygenator 15 through conduit 107.

Subsequently, blood passing from oxygenator 15 along conduit 103 includes leukocyte depleted blood. A portion of the leukocyte depleted blood passing along conduit 103 may be returned to the patient through conduit 104 while another portion is returned to the oxygenator through conduit 102 and the rest of the loop 200. Typically, as part of the protocol described above, blood exiting the loop is passed through another filter assembly, e.g., filter assembly 20, before reaching the patient. Preferably, this additional filter assembly includes a bypass line.

Figure 5:
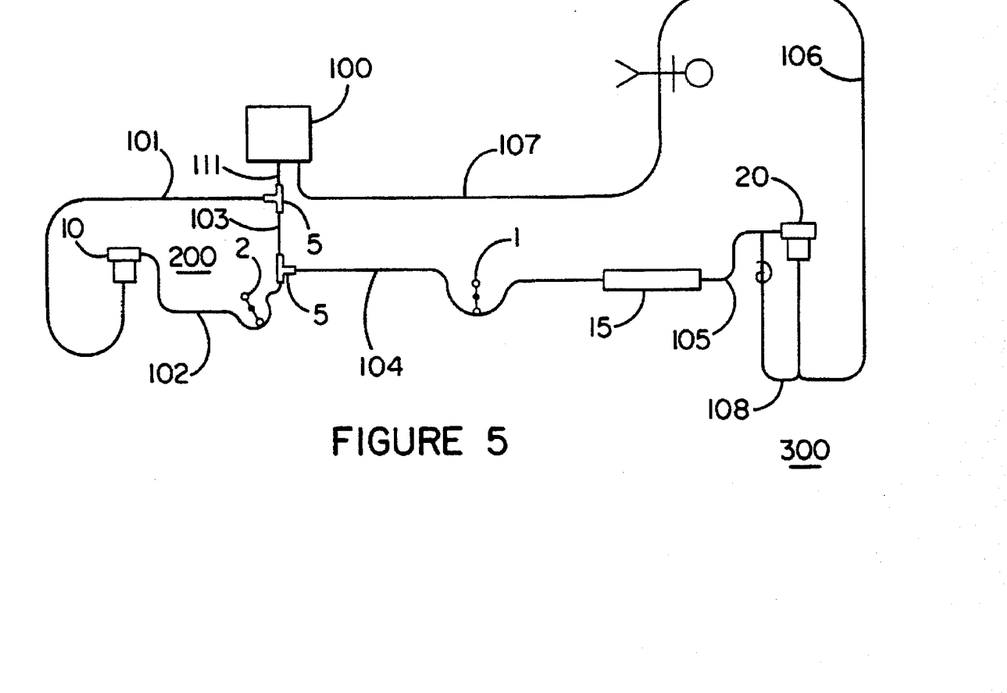
FIG. 5 is another embodiment of a system according to the present invention comprising a recirculation loop including a plurality of three port connectors, and a filter assembly for depleting leukocytes and other undesirable material.

In yet another embodiment, as illustrated in FIG. 5, recirculation loop 200 includes a plurality of conduits 101–103, a connector 5, and a filter assembly 10, as described with respect to, for example, an embodiment corresponding to FIG. 3. However, the embodiment illustrated in FIG. 5 includes an additional three port connector 5 (hereinafter referred to as connector 5' for convenience) and a conduit 111 interposed between container 100 and conduit 103, allowing leukocyte depleted fluid passing along conduit 101 to be passed through the connector 5', and into conduit 103, rather than being passed into container 100 as in FIG. 3. This additional connector 5' may be similar to, or identical to, connector 5 interposed between conduits 102, 103, and 104.

During one extracorporeal treatment protocol, using FIG. 5 for reference, container 100 receives non-leukocyte depleted biological fluid from the patient along conduit 107. With at least pressure differential generator 1 operating, fluid passes from container 100, through the additional conduit 111 and additional connector 5', through conduit 103 and through connector 5. Fluid passing through connector 5 is diverted from the loop 200 into conduit 104, and passed to the patient. With both pressure differential generators 1 and 2 operating, some of the fluid passing from container 100 will be passed to the patient as described above, and some of the fluid passing from the container, through the additional conduit 111 and additional connector 5', through conduit 103 and through connector 5, remains in the loop 200. Accordingly, some of the fluid passing through connector 5 passes through conduit 102, filter assembly 10, conduit 101, and through the additional connector 5' into conduit 103. Since conduit 103 receives non-leukocyte depleted fluid passing from container 100, and leukocyte depleted fluid passing from conduit 101, a mixture of leukocyte depleted and non-leukocyte depleted biological fluid passes along conduit 103.

Accordingly, some of this mixture is passed from conduit 103 through connector 5 and along conduit 104 toward the patient, so that the patient receives some leukocyte depleted fluid. Some of this mixture is passed from conduit 103 through connector 5 and subsequently back to the conduit 103, i.e., through conduit 102, assembly 10, conduit 101, and the additional connector 5'. Since the mixture passing through assembly 10 includes leukocyte depleted and non-leukocyte depleted fluid, some of the mixture becomes more highly depleted of leukocytes.

In another embodiment, the configuration illustrated in FIG. 1 can be modified to include another conduit and three port connector, interposed between container 100 and conduit 103. In this embodiment, one end of conduit 101 is connected to this additional connector, rather than container 100. Accordingly, fluid may be passed from container 100, through the additional conduit and connector, and into conduit 101, and then through assembly 10, conduit 102, connector 5, and conduit 104. In desired, e.g., with only pressure differential generator 1 operating, fluid can be passed from container 100, through the additional conduit and connector, through conduit 103 and connector 5, and through conduit 104 to the patient.

In another embodiment, as illustrated in FIG. 4, a plurality of fluid flow paths between the patient and a container 100 such as a venous reservoir may be provided, so that, if desired, biological fluid may be passed through a leukocyte depletion filter assembly 10 before the fluid is collected in the venous reservoir 100, or the fluid may be collected in the reservoir without passing through the filter assembly 10.

For example, the configuration illustrated in FIG. 4 includes another fluid flow path from conduit 107 to the container 100, and this fluid flow path includes a filter assembly for removing leukocytes 10. Illustratively, this fluid flow path may be placed in communication with container 100 independently of the communication of container 100 with conduit 107. A multi-port connector, e.g., a three port connector 5 such as a T- or Y-connector, interposed between the container 100 and the patient, and connected to conduit 107, allows fluid to be withdrawn from the patient, passed through conduit 112, passed through the connector 5, conduit 109, through the filter assembly 10 and conduit 110, before collecting the leukocyte depleted biological fluid in container 100. The connector 5 also allows biological fluid to be withdrawn from the patient, passed through conduit 107, and collected in container 100, without passing through the fluid flow path including the leukocyte depletion filter assembly. Biological fluid may be passed through either or both fluid flow paths, as desired. In one embodiment, this connector 5 may be similar or identical to connector 5.

Of course, with respect to the configuration illustrated in FIG. 4, should the differential pressure between the inlet and the outlet of this leukocyte depletion filter assembly 10 interposed between the patient and the venous reservoir 100 reach an undesirable level, the other fluid flow path allows fluid to be easily and efficiently passed from the patient to the container without an interruption in flow. In some embodiments, this leukocyte depletion flow path is automatically avoided when the pressure differential reaches a certain level.

In yet another embodiment, a plurality of fluid flow paths between the patient and a container such as a venous reservoir are provided as described above, i.e., wherein one fluid flow path includes a leukocyte depletion filter assembly 10, but the extracorporeal circuit lacks the recirculation loop 200 or 400. For example, with respect to a modification of the configuration of FIG. 4, conduits 101, 102, and 103, as well as connector 5, filter assembly 10, and pressure differential generator 2 may be eliminated, and conduit 104 may be placed in communication with container 100. Similarly, conduits 101 and 102, and assembly 10 can be eliminated from FIG. 2 while including the two fluid flow paths upstream of the container 100 described with respect to FIG. 4. Accordingly, fluid exiting container 100 is passed from the container to the patient.

EXAMPLES

Example 1

An extracorporeal circuit is configured generally as illustrated in FIG. 1. The filter assembly for removing leukocytes 10 comprises a filter element including a fibrous medium arranged in a transparent plastic housing. The fibrous medium, which is produced from polybutylene terephthalate (PBT) fibers, has a CWST of about 66 dynes/cm. The filter assembly, which is produced in accordance with U.S. Pat. No. 5,258,127, has a hold up volume of about 425 ml.

The extracorporeal circuit includes a plurality of plastic tubes or conduits 101–108 providing fluid communication between the other components of the circuit. Filter assemblies 10 and 20 each include a bypass line 108 and a clamp.

As illustrated in FIG. 1, there is a pump 1 upstream of both the oxygenator/heat exchanger 15 and the arterial filter 20, and there is a pump 2 interposed between the venous reservoir 100 and the filter assembly 10.

A T-connector 5 provides fluid communication between the plastic tubing 102 downstream of the filter assembly 10, the tubing 103 downstream of the venous reservoir 100, and the tubing 104 leading to the pump 1.

The extracorporeal circuit includes a sub-circuit or loop 200, which is hereinafter referred to as the recirculation circuit 200. The recirculation circuit 200 provides a fluid flow path from the reservoir 100 along tubing 101 to the filter assembly 10 and back to the reservoir through tubing 102 and 103.

The oxygenator/heat exchanger 15 comprises a membrane oxygenator/heat exchanger. Oxygen is delivered to the oxygenator/heat exchanger through an oxygen filter (not shown).

The arterial filter 20 comprises a filter produced in accordance with U.S. Pat. No. 4,572,724. A plastic tube 108 connecting tubes 105 and 106 provides a bypass to the filter 20. A clamp is associated with the bypass line 108.

The extracorporeal circuit is primed, and then blood is withdrawn from the patient and passed through the circuit and returned to the patient. The pump 2, hereinafter referred to as the recirculation circuit pump 2, is operated at a rate of about 5 liters per minute, and the pump 1 is operated at a rate of about 4 liters per minute. A majority of the leukocyte depleted blood (e.g., about 80%) exiting the leukocyte depleting filter assembly 10 is passed toward the pump 1, and then, via tubing 104, oxygenator 15, tubing 105, arterial filter 20, and tubing 106, back to the patient. A minority of the leukocyte depleted blood exiting the leukocyte depleting filter assembly 10 (e.g., about 20%) is passed back to the venous reservoir 100 via tubing 103. Some blood is flowing through tubing 103 to the reservoir 100 while some blood is flowing through tubing 104. Some of the blood flowing through tubing 103 is recirculated through the recirculation circuit 200, i.e., through tubing 101, assembly 10, tubing 102 and connector 5. Blood continues to recirculate through the circuit 200 over the course of the protocol. Leukocyte depleted blood flowing through tubing 103 into container 200 is mixed, in container 100, with leukocyte containing blood withdrawn from the patient and passed through conduit 107 into container 100.

The circuit is operated for several hours. This example demonstrates that blood can be efficiently leukocyte depleted during an extracorporeal protocol.

Example 2.

An extracorporeal circuit is configured as described in Example 1. The circuit is primed, and pump 1 is operated at a flow rate of about 4 liters per minute for about two hours. During this time, blood is removed from the patient, and is passed through tubing 107, venous reservoir 100, and back to the patient through tubing 103, connector 5, tubing 104, oxygenator 15, tubing 105, arterial filter 20, and tubing 106. During this two hour period, blood is not passed through the leukocyte filter assembly 10.

Just before re-initiating the contractions of the heart, recirculation circuit pump 2 is operated at a flow rate of about 5 liters per minute, thereby directing blood through the leukocyte depletion filter and to the patient. Pump 1 continues to operate at a flow rate of about 4 liters per minute. Accordingly, the blood first delivered to the heart once contractions have begun is leukocyte depleted, which may minimize the "embarrassment" or "shock" to the heart caused by direct exposure to leukocytes.

This example demonstrates that blood can be leukocyte depleted at a desired point in an extracorporeal protocol, e.g., to avoid reperfusion injury before the heart beat is re-established.

Example 3.

An extracorporeal circuit is configured and operated as described in Example 1. However, after about 2 hours, the recirculation circuit pump 2 is shut off, while the pump 1 continues to operate at about 4 liters per minute.

The circuit continues to operate for about an hour.

This example demonstrates that the patient can be easily maintained during an extracorporeal protocol even if the leukocyte depletion circuit fails to operate, e.g., due to the failure of the recirculation circuit pump 2, or if the pump 2 is shut off in the event that the pressure differential between the inlet and outlet of the leukocyte depletion filter assembly 10 reaches an undesirable level.

Example 4.

An extracorporeal circuit is configured and operated as described in Example 1. However, after about 2 hours, the tubing exiting the venous reservoir 100 is clamped upstream of the T connector 5, and the pump 1 is shut off and removed from contact with the tubing between the T-connector 5 and the oxygenator 15.

The circuit continues to operate until the protocol is concluded, about an hour later.

This example demonstrates that the patient can be easily maintained during an extracorporeal protocol even if the pump 1 fails to operate, e.g., due to the failure of the pump.

All of the references cited herein, including publications, patents, and patent applications, are hereby incorporated in their entireties by reference.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

We claim:

1. A method for removing undesirable material including leukocytes from a biological fluid in an extracorporeal circuit comprising:

passing a biological fluid from a patient into a container;

passing a portion of biological fluid from the container through a recirculation loop including a filter assembly for removing leukocytes and back to the container to leukocyte deplete the portion of biological fluid and to pass the leukocyte-depleted biological fluid into the container; and passing a portion of the leukocyte depleted biological fluid from the container to the patient while passing another portion of the leukocyte depleted biological fluid from the container through the recirculation loop.

2. The method of claim 1, wherein the filter assembly is capable of removing leukocytes from the biological fluid at a flow rate of about 1 liter per minute or greater.

3. The method of claim 1, including passing the biological fluid through the recirculation loop at a first rate, and passing the leukocyte depleted biological fluid to the patient at a second rate, wherein the first rate is greater than the second rate.

4. The method of claim 3, wherein the first rate is about 3 liters per minute or greater.

5. A method for removing undesirable material including leukocytes from a biological fluid in an extracorporeal circuit comprising:

passing a leukocyte containing biological fluid from a patient into a container;

passing a portion of biological fluid from the container through a recirculation loop including a filter assembly for removing leukocytes, wherein passing the portion of biological fluid through the recirculation loop provides a leukocyte depleted portion of biological fluid, and includes passing the portion of leukocyte depleted biological fluid into the container;

passing additional leukocyte containing biological fluid from a patient into the container so that the additional fluid is mixed with leukocyte depleted biological fluid in the container to provide a mixture including leukocyte depleted and non-leukocyte depleted biological fluid;

passing the mixture of biological fluid from the container, and passing a portion of the mixture to the patient while passing another portion of the mixture through the recirculation loop and the filter assembly and into the container.

6. The method of claim 5, wherein the filter assembly for removing leukocytes includes a gas plasma treated leukocyte depletion medium.

7. The method of claim 6, including passing biological fluid through the filter assembly at a flow rate of about 1 liter per minute or greater.

8. The method of claim 5, including passing the portion of the mixture through the recirculation loop at a first rate, while passing the portion of the mixture to the patient at a second rate, wherein the first rate is greater than the second rate.

9. A method for processing biological fluid in an extracorporeal circuit comprising:

mixing a non-leukocyte depleted biological fluid with a biological fluid depleted of leukocytes to provide a mixture including leukocyte depleted and non-leukocyte depleted biological fluid;

passing a portion of the mixture to a patient while passing another portion of the mixture through a recirculation loop including a filter assembly for removing leukocytes to provide a portion of biological fluid depleted of leukocytes, and to mix the portion of biological fluid depleted of leukocytes with non-leukocyte depleted biological fluid.

10. The method of claim 9 comprising mixing the non-leukocyte depleted biological fluid with the biological fluid depleted of leukocytes in a container.

11. The method of claim 10, including passing the portion of the mixture through a recirculation loop including a filter assembly for removing leukocytes at a first rate, while passing the portion of the mixture to the patient at a second rate, wherein the first rate is greater than the second rate.

12. The method of claim 9 comprising mixing the non-leukocyte depleted biological fluid with the biological fluid depleted of leukocytes in a conduit.

13. The method of claim 9, including passing the portion of the mixture through a recirculation loop including a filter assembly for removing leukocytes at a first rate, while passing the portion of the mixture to the patient at a second rate, wherein the first rate is different from the second rate.

* * * * *